(12) United States Patent
Zheng et al.

(10) Patent No.: US 12,365,904 B2
(45) Date of Patent: Jul. 22, 2025

(54) THROMBIN BINDING CIRCULAR APTAMER AND USE THEREOF

(71) Applicant: Hefei University of Technology, Anhui (CN)

(72) Inventors: Lei Zheng, Anhui (CN); Yu Mao, Anhui (CN)

(73) Assignee: Hefei University of Technology, Hefei (CN)

( * ) Notice: Subject to any disclaimer, the term of this patent is extended or adjusted under 35 U.S.C. 154(b) by 854 days.

(21) Appl. No.: 17/624,257

(22) PCT Filed: Jan. 22, 2020

(86) PCT No.: PCT/CN2020/073684
§ 371 (c)(1),
(2) Date: Dec. 31, 2021

(87) PCT Pub. No.: WO2021/000584
PCT Pub. Date: Jan. 7, 2021

(65) Prior Publication Data
US 2023/0056099 A1    Feb. 23, 2023

(30) Foreign Application Priority Data
Jul. 3, 2019   (CN) .......................... 201910595164.6

(51) Int. Cl.
| | | |
|---|---|---|
| *C12N 15/115* | (2010.01) | |
| *A61K 31/7088* | (2006.01) | |
| *A61P 1/16* | (2006.01) | |
| *A61P 3/10* | (2006.01) | |
| *A61P 9/14* | (2006.01) | |
| *A61P 13/12* | (2006.01) | |

(52) U.S. Cl.
CPC ........ *C12N 15/115* (2013.01); *C12N 2310/16* (2013.01); *C12N 2310/532* (2013.01); *C12N 2320/30* (2013.01)

(58) Field of Classification Search
None
See application file for complete search history.

(56) References Cited

U.S. PATENT DOCUMENTS

2016/0194641 A1*  7/2016  Kumar ................ C12N 15/115
                                                     536/24.2

OTHER PUBLICATIONS

Di Giusto, Daniel A. et al., Construction, Stability, and Activity of Multivalent Circular Anticoagulant Aptamers*Journal of Biological Chemistry, Nov. 2004, Journal of Biochemistry, vol. 279, Issue 45, pp. 46483-46489 (Year: 2004).*

* cited by examiner

*Primary Examiner* — Anna Skibinsky
*Assistant Examiner* — Catherine L McCormick

(57) ABSTRACT

Provided is a thrombin binding circular aptamer, the nucleotide sequence thereof being at least one selected from a) to e): a) a nucleotide sequence in SEQ ID NO:1, wherein the 5' end and 3' end are connected to form a ring; b) a nucleotide sequence obtained by substitution in the nucleotide sequence in SEQ ID NO:1, the obtained nucleotide sequence being a circular DNA molecule capable of specific recognition of thrombin; c) a nucleotide sequence obtained by deletion in the nucleotide sequence in SEQ ID NO:1, the obtained nucleotide sequence being a circular DNA molecule capable of specific recognition of thrombin; d) a nucleotide sequence obtained by adding one or more nucleotides to the nucleotide sequence in SEQ ID NO:1; and e) a nucleotide sequence obtained by modification of the nucleotide sequence in SEQ ID NO:1 with a chemical group.

7 Claims, 4 Drawing Sheets
Specification includes a Sequence Listing.

SEQUENCE LISTING

```
<160> NUMBER OF SEQ ID NOS: 11

<210> SEQ ID NO 1
<211> LENGTH: 79
<212> TYPE: DNA
<213> ORGANISM: Artificial sequence
<220> FEATURE:
<223> OTHER INFORMATION: Synthetic sequence

<400> SEQUENCE: 1
atctcgacta gtcatagggg gcgcgaacat acgcggttgg tgtggttggc tgacaatact    60 cgttttggt gtctcggat                                                  79

<210> SEQ ID NO 2
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 2
ggttggtgtg gttgg                                                     15

<210> SEQ ID NO 3
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

<222> LOCATION: (1)..(7)
<223> OTHER INFORMATION: n is a, c, g, or t

<400> SEQUENCE: 3
nnnnnnncta gtcatagggg gcgcgaacat acgcggttgg tgtggttggc tgacaatact    60 cgttttggt gtctcggat                                                  79

<210> SEQ ID NO 4
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (8)..(14)
<223> OTHER INFORMATION: n is a, c, g, or t

<400> SEQUENCE: 4
atctcgannn nnntaggggg gcgcgaacat acgcggttgg tgtggttggc tgacaatact    60 cgttttggt gtctcggat                                                  79

<210> SEQ ID NO 5
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (57)..(63)
<223> OTHER INFORMATION: n is a, c, g, or t

<400> SEQUENCE: 5
atctcgacta gtcatagggg gcgcgaacat acgcggttgg tgtggttggc tgacaannnn    60
nnnttttggt gtctcggat                                                 79

<210> SEQ ID NO 6
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (64)..(70)
<223> OTHER INFORMATION: n is a, c, g, or t

<400> SEQUENCE: 6
atctcgacta gtcatagggg gcgcgaacat acgcggttgg tgtggttggc tgacaatact    60
cgtnnnnnnn gtctcggat                                                 79

<210> SEQ ID NO 7
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (71)..(79)
<223> OTHER INFORMATION: n is a, c, g, or t

<400> SEQUENCE: 7
atctcgacta gtcatagggg gcgcgaacat acgcggttgg tgtggttggc tgacaatact    60

-continued

```
cgtttttggt nnnnnnnnn                                              79

<210> SEQ ID NO 8
<211> LENGTH: 72
<212> TYPE: DNA
<213> ORGANISM: Artificial Sequence
<220> FEATURE:
<223> OTHER INFORMATION: Synthetic Sequence

<400> SEQUENCE: 8
atctcgacta gtcataggggg gcgcgaacat acgcggttgg tgtggttggc tgacaatact    60
cgtgtctcgg at                                                         72

<210> SEQ ID NO 9
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 9
atctcgacta gtcataggggg gcgcgaacat acgcggttgg tgtggttggc tgacaatact    60
cgt                                                                   63

<210> SEQ ID NO 10
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 10
atctcgacta gtcataggggg gcgcgaacat acgcggttgg tgtggttggc tgacaa        56

<210> SEQ ID NO 11
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (15)..(34)
<223> OTHER INFORMATION: n is a, c, g, or t
<220> FEATURE:
<221> NAME/KEY: misc_feature
<222> LOCATION: (50)..(69)
<223> OTHER INFORMATION: n is a, c, g, or t

<400> SEQUENCE: 11
atctcgacta gtcannnnnn nnnnnnnnnn nnnnggttgg tgtggttggn nnnnnnnnn      60 nnnnnnnnnt gtctcggat                                                  79
```

THROMBIN BINDING CIRCULAR APTAMER AND USE THEREOF

REFERENCE TO SEQUENCE LISTING

The Substitute Sequence Listing is submitted to replace the previously submitted sequence listing as an ASCII formatted text filed via EFS-Web, with a file name of "Substitute_Sequence_Listing_SCDACH-21002-US-PT.TXT", a creation date of Sep. 22, 2022, and a size of 3,588 bytes. The Substitute Sequence Listing filed via EFS-Web is part of the specification and is incorporated in its entirety by reference herein.

FIELD OF TECHNOLOGY

The present invention belongs to the field of biotechnology, and in particular, to a thrombin binding circular aptamer and use thereof.

BACKGROUND

As a protease present in blood, thrombin plays an important role in a variety of physiological processes, such as blood coagulation, inflammation, and cell signaling. Many studies in recent years have found that thrombin may be used as a biomarker for a variety of diseases as abnormal levels of thrombin in blood may indicate the development of diseases including some liver and kidney diseases, diabetes, thrombophlebitis and cancer. Most drugs specifically targeting thrombin are chemical drugs and monoclonal antibody drugs at present. Chemical drugs may have certain toxic side effects on living organisms due to their poorer biocompatibility. Preparation of monoclonal antibody drugs is organism dependent, which is not only costly but features poor batch-to-batch consistency, and is prone to immunogenicity.

Aptamers are a class of single-stranded DNA or RNA molecules capable of binding targets with high specificity and affinity, and are generally obtained through in vitro screening by systematic evolution of ligands by exponential enrichment (SELEX). The nucleic acid molecules obtained by this "test-tube evolution" method share similarity to antibodies and are capable of specifically binding targets with high affinity. Moreover, aptamers have many advantages over traditional antibodies: (1) aptamers feature excellent stability, are not easily inactivated, and are resistant to thermal denaturation, and capable of folding back into their original conformation at proper temperature; (2) with small molecular weights, aptamers can quickly penetrate tissues, exhibiting no immunogenicity but good biocompatibility; (3) compared to antibodies, aptamers can be screened and synthesized in a more convenient and efficient way, i.e., through in vitro chemical synthesis instead of relying on organisms, which is low in cost, and exhibiting little variation between synthesis batches, and hence can be more widely used. All the properties above make aptamers promising for drug development, drug delivery, targeted therapy, medical detection and diagnosis.

However, the application of aptamers in the biomedical field also faces many challenges, an important one of which is that as nucleic acid-like substances, aptamers are susceptible to degradation by nucleases in complex biological systems, such as blood or organisms, and the half-life of unmodified aptamers in whole blood can be as short as 2 minutes. Therefore, it is essential to improve the resistance of aptamers to nuclease degradation, i.e., to improve the biostability of aptamers, for their practical application in the biomedical filed. The current common practice is chemical modifications of aptamers, but the biocompatibility of chemically modified aptamers are relatively poor. Therefore, it is crucial to provide a thrombin binding aptamer with high biostability and biocompatibility.

SUMMARY

The objective of the present invention is to provide a thrombin binding aptamer with long half-life, high biostability and specificity, and use thereof.

In order to fulfill the above objective, a thrombin binding circular aptamer (TBCA) is provided in a first aspect of the present invention, the nucleotide sequence of the TBCA being at least one selected from a) to d):

a) a nucleotide sequence as shown in SEQ ID NO:1, wherein the 5' end and 3' end are connected to form a ring, the nucleotide sequence as shown in SEQ ID NO:1 being

5'-ATCTCGACTAGTCATAGGGGGCGCGAACATACGCGGTTG

GTGTGGTTGGCTGACAATACTCGTTTTTGGTGTCTCGGAT-3';

b) a nucleotide sequence obtained by substitution in the nucleotide sequence as shown in SEQ ID NO:1, the obtained nucleotide sequence being a circular DNA molecule capable of specific recognition of thrombin, wherein the nucleotide sequence obtained by substitution in the nucleotide sequence as shown in SEQ ID NO:1 has over 80% homology with the SEQ ID NO:1;

c) a nucleotide sequence obtained by deletion in the nucleotide sequence as shown in SEQ ID NO:1, the obtained nucleotide sequence being a circular DNA molecule capable of specific recognition of thrombin, wherein the nucleotide sequence obtained by deletion in the nucleotide sequence as shown in SEQ ID NO:1 has over 70% homology with the nucleotide sequence as shown in SEQ ID NO:1;

d) a nucleotide sequence obtained by adding one or more nucleotides to the nucleotide sequence as shown in SEQ ID NO:1, the obtained nucleotide sequence being a circular DNA molecule capable of specific recognition of thrombin, wherein the nucleotide sequence obtained by adding one or more nucleotides to the nucleotide sequence as shown in ID NO:1 has over 80% homology with the nucleotide sequence as shown in SEQ ID NO:1;

e) a nucleotide sequence obtained by modification in the nucleotide sequence as shown in SEQ ID NO: 1 with a chemical group.

More particularly, both the nucleotide sequence obtained by substitution in the nucleotide sequence as shown in SEQ ID NO:1 and the nucleotide sequence obtained by deletion in the nucleotide sequence as shown in SEQ ID NO:1 have the nucleotide sequence as shown in SEQ ID NO:8.

In particular, the nucleotide sequence obtained by substitution in the nucleotide sequence as shown in SEQ ID NO:1 has over 85% homology with the SEQ ID NO:1.

More particularly, the nucleotide sequence obtained by substitution in the nucleotide sequence as shown in SEQ ID NO:1 has over 90% homology with the SEQ ID NO:1.

More particularly, the nucleotide sequence obtained by substitution in the nucleotide sequence as shown in SEQ ID NO:1 has over 95% homology with the SEQ ID NO:1.

More particularly, the nucleotide sequence obtained by substitution in the nucleotide sequence as shown in SEQ ID NO:1 has over 98% homology with the SEQ ID NO:1.

More particularly, the nucleotide sequence obtained by substitution in the nucleotide sequence as shown in SEQ ID NO:1 comprises at least one from b1) to b5):

b1) a nucleotide sequence as shown in SEQ ID NO:3, the nucleotide sequence as shown in SEQ ID NO:3 being

5'-NNNNNNNNCTAGTCATAGGGGCGCGAACATACGCGGTTGG

TGTGGTTGGCTGACAATACTCGTTTTTGGTGTCTCGGAT-3';

b2) a nucleotide sequence as shown in SEQ ID NO:4, the nucleotide sequence as shown in SEQ ID NO:4 being

5'-ATCTCGANNNNNNNNTAGGGGCGCGAACATACGCGGTTGG

TGTGGTTGGCTGACAATACTCGTTTTTGGTGTCTCGGAT-3';

b3) a nucleotide sequence as shown in SEQ ID NO:5, the nucleotide sequence as shown in SEQ ID NO:5 being

5'-ATCTCGACTAGTCATAGGGGCGCGAACATACGCGGTTGGTGTGGTT

GGCTGACAANNNNNNNTTTTGGTGTCTCGGAT-3';

b4) a nucleotide sequence as shown in SEQ ID NO:6, the nucleotide sequence as shown in SEQ ID NO:6 being

5'-ATCTCGACTAGTCATAGGGGCGCGAACATACGCGGTTGGTGTGGTT

GGCTGACAATACTCGTNNNNNNNNGTCTCGGAT-3;

b5) a nucleotide sequence as shown in SEQ ID NO:7, the nucleotide sequence as shown in SEQ ID NO:7 being

5'-ATCTCGACTAGTCATAGGGGCGCGAACATACGCGGTTGGTGTGGTT

GGCTGACAATACTCGTTTTTGGTNNNNNNNNNN-3;

wherein, the N represents at least one from A, T, C and G.

More particularly, the N represents T and/or A.

More particularly, the nucleotide sequence obtained by deletion in the nucleotide sequence as shown in SEQ ID NO:1 has over 75% homology with the SEQ ID NO:1.

More particularly, the nucleotide sequence obtained by deletion in the nucleotide sequence as shown in SEQ ID NO:1 has over 80% homology with the SEQ ID NO:1.

More particularly, the nucleotide sequence obtained by deletion in the nucleotide sequence as shown in SEQ ID NO:1 has over 90% homology with the SEQ ID NO:1.

More particularly, the nucleotide sequence obtained by deletion in the nucleotide sequence as shown in SEQ ID NO:1 has over 95% homology with the SEQ ID NO:1.

In particular, the nucleotide sequence obtained by deletion in the nucleotide sequence as shown in SEQ ID NO:1 comprises at least one from c1) to c3):

c1) a nucleotide sequence as shown in SEQ ID NO:8, the nucleotide sequence as shown in SEQ ID NO:8 being

5'-ATCTCGACTAGTCATAGGGGCGCGAACATACGCGGTTGGTGTGGTT

GGCTGACAATACTCGTGTCTCGGAT-3';

c2) a nucleotide sequence as shown in SEQ ID NO:9, the nucleotide sequence as shown in SEQ ID NO:9 being

5'-ATCTCGACTAGTCATAGGGGCGCGAACATACGCGGTTGGTGTGGTT

GGCTGACAATACTCGT-3;

c3) a nucleotide sequence as shown in SEQ ID NO:10, the nucleotide sequence as shown in SEQ ID NO:10 being

5'-ATCTCGACTAGTCATAGGGGCGCGAACATACGCGGTTGGTGTGGTT

GGCTGACAA-3'.

In particular, the nucleotide sequence obtained by adding one or more nucleotides to the nucleotide sequence as shown in SEQ ID NO:1 has over 90% homology with the SEQ ID NO:1.

More particularly, the nucleotide sequence obtained by adding one or more nucleotides to the nucleotide sequence as shown in SEQ ID NO:1 has over 95% homology with the SEQ ID NO:1.

More particularly, the nucleotide sequence obtained by adding one or more nucleotides to the nucleotide sequence as shown in SEQ ID NO:1 has over 98% homology with the SEQ ID NO:1.

Particularly, the chemical group comprises: —$NH_2$ or —F modified at the 2'-position of a pyrimidine ring, —$OCH_3$ modified at the 2'-position of a purine ring, a phosphorothioate radical modified between adjacent nucleotides, and a pyrimidine analogue modified at the 5' endpoint.

More particularly, the pyrimidine analogue is uridine.

Provided in a second aspect of the present invention is an use of the above-mentioned thrombin binding circular aptamer in preparation of thrombin inhibitors.

Provided in a third aspect of the present invention is an use of the above-mentioned thrombin binding circular aptamer in preparation of drug products for prevention and/or treatment of diseases associated with thrombin. Diseases associated with thrombin include: diseases associated with liver damage, diseases related to kidney failure, diabetes and thrombophlebitis among others.

The thrombin binding circular aptamer of the present invention is capable of specific recognition of thrombin, and human α-thrombin in particular. By removal of nucleic-acid molecular endpoints, the thrombin binding circular aptamer is not affected by the exocytosis of exonuclease, thereby showing high biostability and biocompatibility with a half-life of up to 8 hours at 37° C. in 50% serum.

The thrombin binding circular aptamer of the present invention may be used in preparation of thrombin inhibitors with excellent efficacy.

The thrombin binding circular aptamer of the present invention may be used in preparation of drug products for prevention and/or treatment of diseases associated with thrombin with excellent efficacy.

Other features and advantages of the invention will be described in detail in the detailed description which follows.

BRIEF DESCRIPTION OF DRAWINGS

A more detailed description of exemplary embodiments of the present invention is provided in combination with drawings to demonstrate more clearly the above-mentioned and other objectives, features and advantages of the present invention.

DETAILED DESCRIPTION OF THE EMBODIMENTS

Preferred embodiments of the present invention will be described in more detail below. While the present invention has been described in terms of the preferred embodiments of the present invention, it should be understood that the present invention may be embodied in a variety of forms and should not be limited by the embodiments set forth herein.

See Table 1 for the nucleotide sequences of the DNA molecules used in the embodiments hereinafter:

TABLE 1

| Nucleotide sequences of DNA molecules | | |
|---|---|---|
| Sequence Name | Sequence Number | Oligonucleotide Sequence |
| TBCA | SEQ ID NO: 1 | 5'-ATCTCGACTAGTCATAGGGGCGCGAACATACGCGGTTGGT GTGGTTGGCTGACAATACTCGTTTTTGGTGTCTCGGAT-3' |
| TBA | SEQ ID NO: 2 | 5'-GGTTGGTGTGGTTGG-3' |
| M1 | SEQ ID NO: 3 | 5'-NNNNNNNCTAGTCATAGGGGCGCGAACATACGCGGTTGGT GTGGTTGGCTGACAATACTCGTTTTTGGTGTCTCGGAT-3' |
| M2 | SEQ ID NO: 4 | 5'-ATCTCGANNNNNNNNTAGGGGCGCGAACATACGCGGTTGGT GTGGTTGGCTGACAATACTCGTTTTTGGTGTCTCGGAT-3' |
| M3 | SEQ ID NO: 5 | 5'-ATCTCGACTAGTCATAGGGGCGCGAACATACGCGGTTGGT GTGGTTGGCTGACAANNNNNNNNTTTTGGTGTCTCGGAT-3' |
| M4 | SEQ ID NO: 6 | 5'-ATCTCGACTAGTCATAGGGGCGCGAACATACGCGGTTGGT GTGGTTGGCTGACAATACTCGTNNNNNNNNGTCTCGGAT-3' |
| M5 | SEQ ID NO: 7 | 5'-ATCTCGACTAGTCATAGGGGCGCGAACATACGCGGTTGGT GTGGTTGGCTGACAATACTCGTTTTTGGTNNNNNNNNN-3' |
| D1 | SEQ ID NO: 8 | 5'-ATCTCGACTAGTCATAGGGGCGCGAACATACGCGGTTGGT GTGGTTGGCTGACAATACTCGTGTCTCGGAT-3' |
| D2 | SEQ ID NO: 9 | 5'-ATCTCGACTAGTCATAGGGGCGCGAACATACGCGGTTGGT GTGGTTGGCTGACAATACTCGT-3' |
| D3 | SEQ ID NO: 10 | 5'-ATCTCGACTAGTCATAGGGGCGCGAACATACGCGGTTGGT GTGGTTGGCTGACAA-3' |
| Random circular nucleic acid (Lib) | SEQ ID NO: 11 | 5'-ATCTCGACTAGTCANNNNNNNNNNNNNNNNNNNNGGTTGGT GTGGTTGGNNNNNNNNNNNNNNNNNNNNNTGTCTCGGAT-3' |

N in Table 1 represents a random nucleotide.

Embodiment 1

This present embodiment is provided to demonstrate that the thrombin binding circular aptamer (TBCA) of the present invention has a long half-life and a high biostability.

Figure 1:
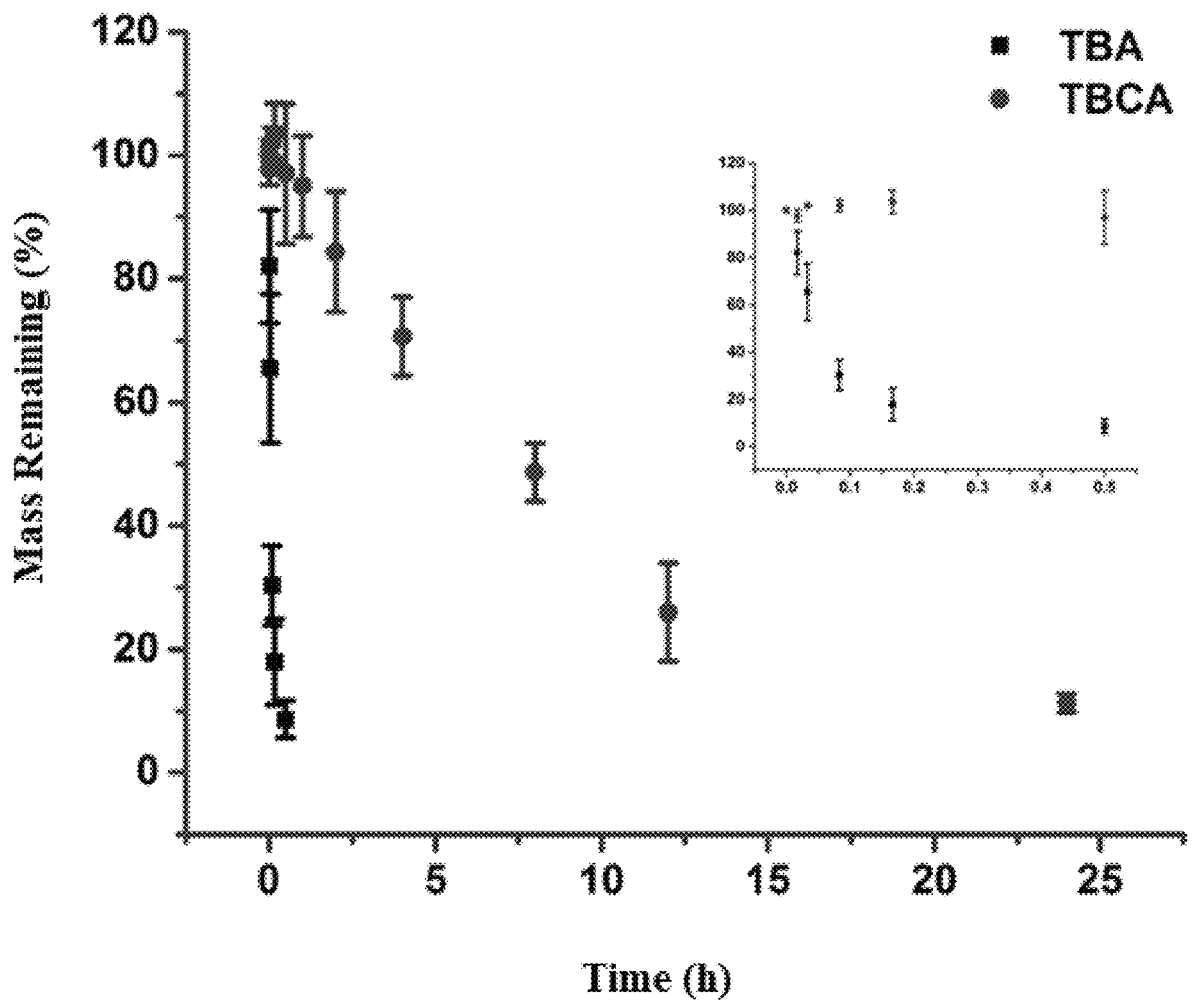
FIG. 1 shows the results of incubation of TBCA and thrombin binding aptamer (TBA) for different periods of time.

Incubation of 0.5 μM of TBCA and TBA each (nucleotide sequences thereof are shown in SEQ ID NO:1 and SEQ ID NO:2, respectively) was performed in 50% serum at a temperature of 37° C. Samples were taken for electrophoresis at 0 min, 1 min, 2 min, 5 min, 10 min, 30 min, 60 min (1 h), 120 min (2 h), 240 min (4 h), 480 min (8 h), 720 min (12 h) and 1440 min (24 h), respectively. The gray values of the electrophoretic bands were analyzed at the end and the results are shown in FIG. 1. FIG. 1 shows the mass remaining of TBCA and TBA after incubation together in 50% serum at 37° C. for a certain amount of time. As shown in FIG. 1, the half-life of TBA was approximately 2 min, whereas the half-life of TBCA was up to about 8 hours. It is hence demonstrated that the biostability of TBCA is significantly higher than that of TBA.

Embodiment 2

The present embodiment is provided to demonstrate that TBCA is capable of specific recognition of thrombin and has a highly efficient inhibition of thrombin.

Thrombin (0.1 nM) and fibrinogen (2 μM) were incubated with TBCA and Lib of different concentrations separately in buffer systems (total reaction volume of 100 μL) for a certain amount of time (till reaction equilibrium was reached), and the $IC_{50}$ values of TBCA and Lib were calculated by fitting of the absorbance of the reaction system measured at 350 nm on a microplate reader.

Figure 2:
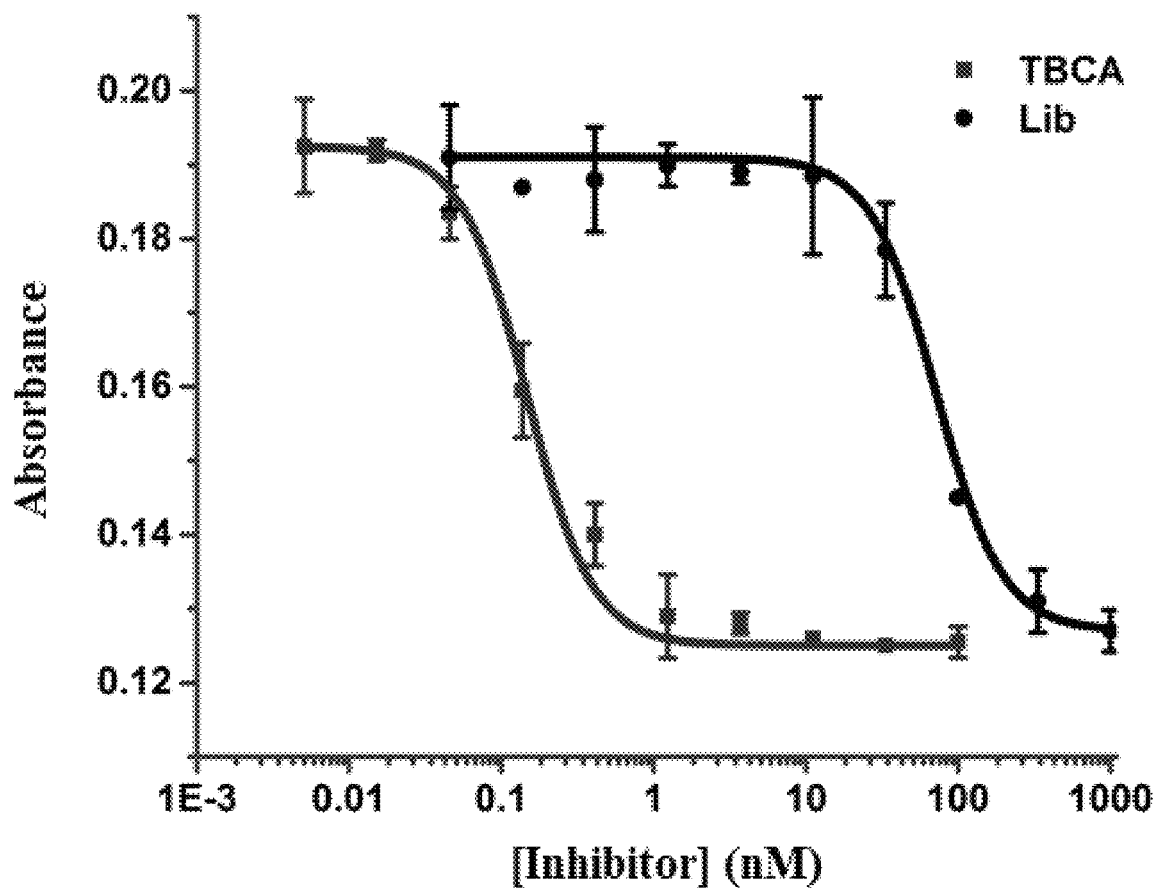
FIG. 2 shows the results of inhibition of thrombin by the TBCA of the present invention and a random circular nucleic acid.

The inhibition of thrombin-catalyzed conversion of fibrinogen to fibrin by TBCA and the random circular nucleic acid (Lib) was compared. Please refer to FIG. 2 for the results of inhibition of thrombin by the TBCA of the present invention and the random circular nucleic acid. As shown in FIG. 2, at a thrombin concentration of 0.1 nM, the $IC_{50}$ of TBCA was 0.15 nM, whereas the $IC_{50}$ of Lib was 72.14 nM. It is hence demonstrated that the inhibition of thrombin by TBCA is significantly better than that by the random circular nucleic acid (Lib).

Embodiment 3

The present embodiment is provided to demonstrate that the thrombin binding circular aptamer (TBCA) of the present invention has an efficient inhibition of thrombin.

Thrombin (0.1 nM) and fibrinogen (2 μM) were incubated with TBCA, M1, M2, M3, M4, M5, D1, D2 and D3 of different concentrations separately in buffer systems (total reaction volume of 100 μL) for a certain amount of time (till reaction equilibrium was reached), and the $IC_{50}$ values of TBCA, M1, M2, M3, M4, M5, D1, D2 and D3 were calculated by fitting of the absorbance of the reaction system measured at 350 nm on a microplate reader.

Figure 3:
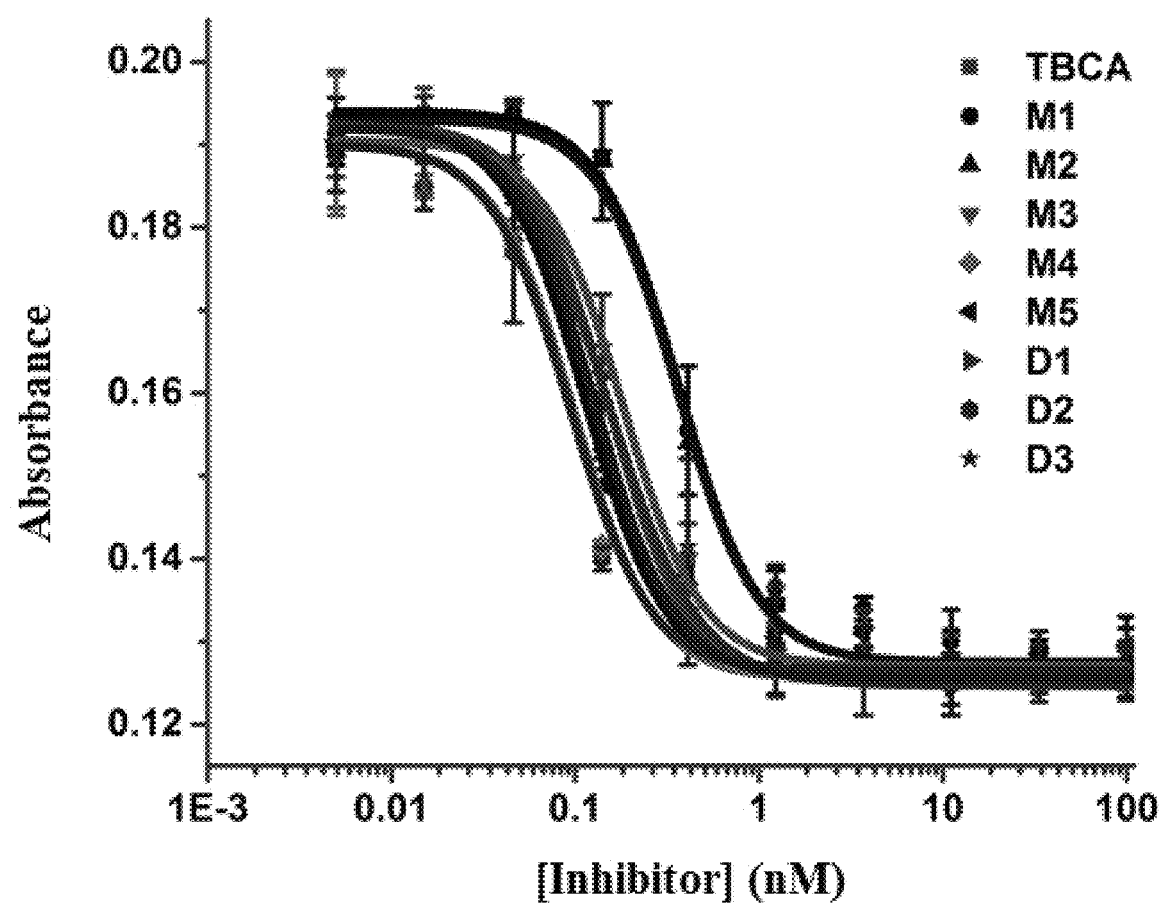
FIG. 3 shows the results of inhibition of thrombin by the TBCA of the present invention.

Please refer to FIG. 3 for the results of inhibition of thrombin by the TBCA of the present invention. As shown in FIG. 3, at a thrombin concentration of 0.1 nM, the $IC_{50}$ values of TBCA, M1, M2, M3, M4, M5, D1, D2 and D3 were 0.15 nM, 0.37 nM, 0.36 nM, 0.18 nM, 0.10 nM, 0.11 nM, 0.15 nM, 0.09 nM and 0.13 nM, respectively. It is hence demonstrated that, the thrombin binding circular aptamer (TBCA) of the present invention is capable of specific recognition of thrombin and has an efficient inhibition of thrombin.

Embodiment 4

The present embodiment is provided to demonstrate that the thrombin binding circular aptamer (TBCA) of the present invention has a more efficient inhibition of thrombin compared to existing thrombin inhibitors.

Thrombin (0.1 nM) and fibrinogen (2 μM) were incubated with TBCA, TBA and Argatroban of different concentrations separately in buffer systems (total reaction volume of 100 μL) for a certain amount of time (till reaction equilibrium was reached), and the $IC_{50}$ values of TBCA, TBA and Argatroban were calculated by fitting of the absorbance of the reaction system measured at 350 nm on a microplate reader.

Figure 4:
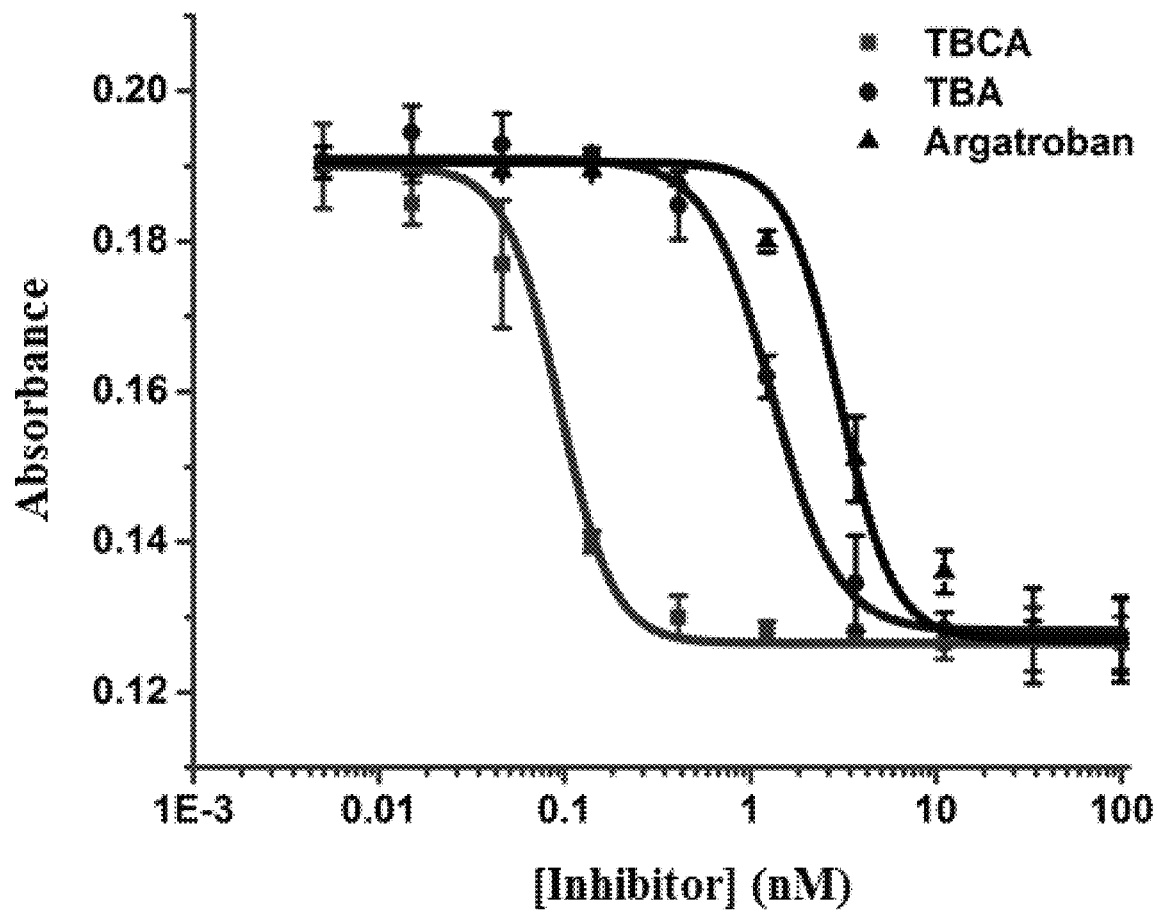
FIG. 4. shows the results of inhibition of thrombin by the TBCA of the present invention and an existing thrombin inhibitor Argatroban.

Please refer to FIG. 4 for the results of inhibition of thrombin by the TBCA of the present invention and the existing thrombin inhibitors, wherein the existing thrombin inhibitors were TBA and Argatroban, respectively. As shown in FIG. 4, the inhibition of thrombin by TBCA was significantly better than that by the existing thrombin binding aptamer and the anticoagulant chemical drug. TBCA, TBA that specifically targets α-thrombin, and Argatroban, a currently commonly used anticoagulant that specifically targets thrombin, were used as examples to determine the $IC_{50}$ values by measuring the inhibition of thrombin-catalyzed conversion of fibrinogen to fibrin by these anticoagulants. At a thrombin concentration of 0.1 nM, the $IC_{50}$ values of TBA and Argatroban were 1.3 nM and 3.0 nM, respectively, demonstrating that the inhibition effect on thrombin of TBCA was 13 times as high as that of the existing TBA that specifically targets α-thrombin, and 30 times as high as that of Argatroban.

The embodiments of the present invention have been described above, and the foregoing description is illustrative, not limiting, and not limited to the disclosed embodiments. Numerous modifications and changes will be apparent to those skilled in the art without departing from the scope and spirit of the illustrated embodiments.

What is claimed is:

1. A thrombin binding circular aptamer, characterized in that, the thrombin binding circular aptamer has a nucleotide sequence of at least one selected from a) to e):
   a) a nucleotide sequence as shown in SEQ ID NO:1, wherein the 5' end and 3' end are connected to form a ring, the nucleotide sequence as shown in SEQ ID NO:1 being 5'-ATCTCGACTAGTCATAGGGGCGCGAACATACGCGGTTGGTGTGGT
   TGGCTGACAATACTCGTTTTTGGTGTCTCGGAT-3';

b) a nucleotide sequence obtained by substitution in the nucleotide sequence as shown in SEQ ID NO:1, the obtained nucleotide sequence being a circular DNA molecule capable of specific recognition of thrombin, wherein the nucleotide sequence obtained by substitution in the nucleotide sequence as shown in SEQ ID NO:1 has over 80% homology with the SEQ ID NO:1;
   c) a nucleotide sequence obtained by deletion in the nucleotide sequence as shown in SEQ ID NO:1, the obtained nucleotide sequence being a circular DNA molecule capable of specific recognition of thrombin, wherein the nucleotide sequence obtained by deletion in the nucleotide sequence as shown in SEQ ID NO:1 has over 70% homology with the nucleotide sequence as shown in SEQ ID NO:1;
   d) a nucleotide sequence obtained by adding one or more nucleotides to the nucleotide sequence as shown in SEQ ID NO:1, the obtained nucleotide sequence being a circular DNA molecule capable of specific recognition of thrombin, wherein the nucleotide sequence obtained by adding one or more nucleotides to the nucleotide sequence as shown in SEQ ID NO:1 has over 80% homology with the nucleotide sequence as shown in SEQ ID NO:1;
   e) a nucleotide sequence obtained by modification of the nucleotide sequence as shown in SEQ ID NO:1 with a chemical group.

2. The thrombin binding circular aptamer according to claim 1, characterized in that, the nucleotide sequence obtained by substitution in the nucleotide sequence as shown in SEQ ID NO:1 has over 90% homology with the SEQ ID NO:1.

3. The thrombin binding circular aptamer according to claim 1, characterized in that, the nucleotide sequence obtained by substitution in the nucleotide sequence as shown in SEQ ID NO:1 comprises at least one from b1) to b5):
   b1) a nucleotide sequence as shown in SEQ ID NO:3, the nucleotide sequence as shown in SEQ ID NO:3 being 5'-NNNNNNNNCTAGTCATAGGGGCGCGAACATACGCGGTTGGTGTGGT
   TGGCTGACAATACTCGTTTTTGGTGTCTCGGAT-3';

b2) a nucleotide sequence as shown in SEQ ID NO:4, the nucleotide sequence as shown in SEQ ID NO:4 being 5'-ATCTCGANNNNNNNNTAGGGGGCGCGAACATACGCGGTTGGTGTGGT
   TGGCTGACAATACTCGTTTTTGGTGTCTCGGAT-3';

b3) a nucleotide sequence as shown in SEQ ID NO:5, the nucleotide sequence as shown in SEQ ID NO:5 being 5'-ATCTCGACTAGTCATAGGGGCGCGAACATACGCGGTTGGTGTGGTT
   GGCTGACAANNNNNNNTTTTGGTGTCTCGGAT-3';

b4) a nucleotide sequence as shown in SEQ ID NO:6, the nucleotide sequence as shown in SEQ ID NO:6 being 5'-ATCTCGACTAGTCATAGGGGCGCGAACATACGCGGTTGGTGTGGT
   TGGCTGACAATACTCGTNNNNNNNNGTCTCGGAT-3';

b5) a nucleotide sequence as shown in SEQ ID NO:7, the nucleotide sequence as shown in SEQ ID NO:7 being 5'-ATCTCGACTAGTCATAGGGGCGCGAACATACGCGGTTGGTGTGGTT
   GGCTGACAATACTCGTTTTTGGTNNNNNNNNN-3';

wherein, N represents at least one from A, T, C and G.

4. The thrombin binding circular aptamer according to claim 3, characterized in that, the N represents T and/or A.

5. The thrombin binding circular aptamer according to claim 1, characterized in that, the nucleotide sequence obtained by deletion in the nucleotide sequence as shown in SEQ ID NO:1 has over 80% homology with the SEQ ID NO:1.

6. The thrombin binding circular aptamer according to claim 1, characterized in that, the nucleotide sequence obtained by deletion in the nucleotide sequence as shown in SEQ ID NO:1 comprises at least one from c1) to c3):
   c1) a nucleotide sequence as shown in SEQ ID NO:8, the nucleotide sequence as shown in SEQ ID NO:8 being 5'-ATCTCGACTAGTCATAGGGGCGCGAACATACGCGGTTGGTGTGGTT
   GGCTGACAATACTCGTGTCTCGGAT-3';

c2) a nucleotide sequence as shown in SEQ ID NO:9, the nucleotide sequence as shown in SEQ ID NO:9 being

5'-ATCTCGACTAGTCATAGGGGCGCGAACATACGCGGTTGGTGTGGTT
   GGCTGACAATACTCGT-3';

c3) a nucleotide sequence as shown in SEQ ID NO:10, the nucleotide sequence as shown in SEQ ID NO:10 being

5'-ATCTCGACTAGTCATAGGGGCGCGAACATACGCGGTTGGTGTGGTTG
   GCTGACAA-3'.

7. The thrombin binding circular aptamer according to claim 1, characterized in that, the chemical group comprises: —NH$_2$ or —F modified at the 2'-position of a pyrimidine ring, —OCH$_3$ modified at the 2'-position of a purine ring, a phosphorothioate radical modified between adjacent nucleotides, and a pyrimidine analogue modified at the 5'-endpoint.

* * * * *